US009290477B2

(12) United States Patent
Venkatraman et al.

(10) Patent No.: US 9,290,477 B2
(45) Date of Patent: Mar. 22, 2016

(54) INHIBITORS OF β-SECRETASE

(71) Applicant: Vitae Pharmaceuticals, Inc., Fort Washington, PA (US)

(72) Inventors: Shankar Venkatraman, Lansdale, PA (US); Jing Yuan, Lansdale, PA (US); Yajun Zheng, Hockessin (DE)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 14/431,588

(22) PCT Filed: Sep. 25, 2013

(86) PCT No.: PCT/US2013/061592
§ 371 (c)(1),
(2) Date: Mar. 26, 2015

(87) PCT Pub. No.: WO2014/052398
PCT Pub. Date: Apr. 3, 2014

(65) Prior Publication Data
US 2015/0259325 A1 Sep. 17, 2015

Related U.S. Application Data

(60) Provisional application No. 61/706,957, filed on Sep. 28, 2012.

(51) Int. Cl.
*A61K 31/4184* (2006.01)
*C07D 235/02* (2006.01)
*C07D 401/12* (2006.01)
*C07D 401/04* (2006.01)

(52) U.S. Cl.
CPC ............ *C07D 401/12* (2013.01); *C07D 235/02* (2013.01); *C07D 401/04* (2013.01)

(58) Field of Classification Search
USPC ................... 548/301.1; 514/393, 278; 546/15
See application file for complete search history.

(56) References Cited

U.S. PATENT DOCUMENTS

| 4,874,869 | A | 10/1989 | Ueda et al. |
| 5,430,048 | A | 7/1995 | Gadwood |
| 7,423,158 | B2 | 9/2008 | Malamas et al. |
| 7,607,246 | B2 | 10/2009 | Valiyambath Krishnan et al. |
| 7,872,009 | B2 | 1/2011 | Albrecht et al. |
| 8,415,483 | B2 * | 4/2013 | Csjernyik et al. ......... 548/301.1 |
| 8,426,447 | B2 | 4/2013 | White et al. |
| 8,450,308 | B2 | 5/2013 | Dillard et al. |
| 8,633,212 | B2 | 1/2014 | Cacatian et al. |
| 8,889,703 | B2 | 11/2014 | Dillard et al. |
| 8,921,359 | B2 | 12/2014 | Dillard et al. |
| 8,981,112 | B2 | 3/2015 | Bukhtiyarov et al. |
| 9,018,391 | B2 | 4/2015 | Bukhtiyarov et al. |
| 9,045,500 | B2 | 6/2015 | Dillard et al. |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0281730 | A1 | 12/2006 | Zhu et al. |
| 2006/0287294 | A1 | 12/2006 | Zhu et al. |
| 2007/0004730 | A1 | 1/2007 | Zhou et al. |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0203116 | A1 | 8/2007 | Quagliato et al. |
| 2007/0287692 | A1 | 12/2007 | Wu et al. |
| 2009/0209529 | A1 | 8/2009 | Andreini et al. |
| 2011/0071126 | A1 | 3/2011 | Cacatian et al. |
| 2011/0152253 | A1 | 6/2011 | Motoki et al. |
| 2011/0218192 | A1 | 9/2011 | Dillard et al. |
| 2012/0065195 | A1 | 3/2012 | Clark et al. |
| 2013/0053377 | A1 | 2/2013 | Dillard et al. |
| 2013/0289050 | A1 | 10/2013 | Bukhtiyarov et al. |
| 2013/0317014 | A1 | 11/2013 | Dillard et al. |
| 2014/0057927 | A1 | 2/2014 | Bukhtiyarov et al. |
| 2014/0200223 | A1 | 7/2014 | Cacatian et al. |
| 2015/0031691 | A1 | 1/2015 | Dillard et al. |
| 2015/0150872 | A1 | 6/2015 | Bukhtiyarov et al. |
| 2015/0239849 | A1 | 8/2015 | Bukhtiyarov et al. |

FOREIGN PATENT DOCUMENTS

| WO | 9305045 | A1 | 3/1993 |
| WO | 9530642 | A1 | 11/1995 |
| WO | 2005058311 | A1 | 6/2005 |
| WO | 2006044497 | A2 | 4/2006 |
| WO | 2006065277 | A2 | 6/2006 |
| WO | 2007016012 | A2 | 2/2007 |
| WO | 2007038271 | A1 | 4/2007 |

(Continued)

OTHER PUBLICATIONS

CA 149:307845 (Sep. 2008).
Caplus 2008:1339943 (Nov. 2008).
Gadwood et al. "Synthesis and Biological Activity of Spirocyclic Benzopyran Imidazolone Potassium Channel Openers," J. Med. Chem., vol. 36(10):1480-1487 (1993).
Hunt, Kevin W., et al, Spirocyclic Beta Site Amyloid Precursor Protein Cleaving Enzyme 1 (BACE1) Inhibitors: From Hit to Lowering of Cerebrospinal Fluid (CSF) Amyloid Beta in a Higher Species, Journal of Medicinal Chemistry 56(8):3379-3403 (2013).

(Continued)

*Primary Examiner* — Charanjit Aulakh
(74) *Attorney, Agent, or Firm* — McCarter & English, LLP; Steven G. Davis; Xin Zhang

(57) ABSTRACT

The present invention relates to spirocyclic indane imidazole 4-amines and their use as inhibitors of the β-secretase enzyme (BACE1) activity, pharmaceutical compositions containing the same, and methods of using the same as therapeutic agents in the treatment of neurodegenerative disorders, disorders characterized by cognitive decline, cognitive impairment, dementia and diseases characterized by production of β-amyloid aggregates.

18 Claims, No Drawings

(56) References Cited

FOREIGN PATENT DOCUMENTS

| | | | |
|---|---|---|---|
| WO | 2007049532 A1 | 5/2007 |
| WO | 2007063114 A2 | 6/2007 |
| WO | 2007076284 A2 | 7/2007 |
| WO | 2007078813 A2 | 7/2007 |
| WO | 2007100536 A1 | 9/2007 |
| WO | 2008010481 A1 | 1/2008 |
| WO | 2008030412 A2 | 3/2008 |
| WO | 2008076043 A1 | 6/2008 |
| WO | 2008076044 A1 | 6/2008 |
| WO | 2008076045 A1 | 6/2008 |
| WO | 2008076046 A1 | 6/2008 |
| WO | 2008103351 A2 | 8/2008 |
| WO | 2008115552 A1 | 9/2008 |
| WO | 2008118379 A2 | 10/2008 |
| WO | 2008133273 A1 | 11/2008 |
| WO | 2008133274 A1 | 11/2008 |
| WO | 2008150217 A1 | 12/2008 |
| WO | 2009134617 A1 | 11/2009 |
| WO | 2010013302 A1 | 2/2010 |
| WO | 2010013794 A1 | 2/2010 |
| WO | 2010021680 A2 | 2/2010 |
| WO | 2010/058333 A1 | 5/2010 |
| WO | 2010105179 A2 | 9/2010 |
| WO | 2011072064 A1 | 6/2011 |
| WO | 2011106414 A1 | 9/2011 |
| WO | 2012087237 A1 | 6/2012 |
| WO | 2013134085 A1 | 9/2013 |
| WO | 2014035860 A1 | 3/2014 |

OTHER PUBLICATIONS

International Search Report for related PCT/US2009/004686; Feb. 12, 2010.
Written Opinion for related PCT/US2009/004686; Feb. 12, 2010.
International Search Report for related PCT/US2010/027173; Sep. 6, 2010.
Written Opinion for related PCT/US2010/027173; Sep. 6, 2010.
International Search Report for related PCT/US2011/025912: Apr. 1, 2011.
Written Opinion for related PCT/US2011/025912: Apr. 1, 2011.
International Search Report for related PCT/US2013/028796: May 3, 2013.
Written Opinion for related PCT/US2011/028796: May 3, 2013.
International Search Report for related PCT/US2013/056566 mailed Nov. 8, 2013.
Written Opinion for related PCT/US2013/056566 mailed Nov. 8, 2013.
Michael S. Malamas et al., Aminoimidazoles as Potent and Selective Human Beta-Secretase (BACE1) Inhibitors; J. Med. Chem. (2009), 52, 6314-6323.
Michael S. Malamas et al.; Design and Synthesis of 5,5'-Disubstituted Aminohydantoins as Potent and Selective Human Beta-Secretase (BACE1) Inhibitors; J. Med. Chem. (2010), 53, 1146-1158.
Michael S. Malamas; Di-substituted pyridinyl aminohydantoins as potent and highly selective human Beta-secretase (BACE1) inhibitors; Bioorganic & Medicinal Chemistry 18 (2010) 630-639.
Pawel Nowak et al.; Discovery and initial optimization of 5,50-disubstituted aminohydantoins as potent b-secretase (BACE1) inhibitors; Bioorganic & Medicinal Chemistry Letters 20 (2010) 632-635.
R. Silvestri, "Boom in the Developemnt of Non-Peptidic β-Secretase (MACE1) Inhibitors for the Treatment of Alzheimer's Disease", Medicinal Research Reviews, (2009), vol. 29, No. 2, 295-338.
Yu-Sen Wang et al.; Application of Fragment-BasedNMR Screening, X-ray Crystallography, Structure-Based Design, and Focused Chemical Library Design to Identify Novel MicroM Leads for the Development of nM BACE-1 ( Beta-Site APP Cleaving Enzyme 1) Inhibitors; J. Med. Chem. (2010), 53, 942-950.
Zhaoning Zhu et al.; Discovery of Cyclic Acylguanidines as Highly Potent and Selective Beta-Site Amyloid Cleaving Enzyme (BACE) Inhibitors: Part I Inhibitor Design and Validation; J. Med. Chem. (2010), 53, 951-965.
International Preliminary Report on Patentability for related International Patent Application No. PCT/US2013/056566, Dated: Aug. 19, 2014.
International Search Report and Written Opinion for related International Application No. PCT/US2013/061592, Dated: Dec. 17, 2013.
International Preliminary Report on Patentability for related International Application No. PCT/US2013/061592, Dated: Mar. 31, 2015.
Huang et al, "Pharmacaphore Model Construction of β-Secretase Inhibitors", Acta Chimica Sinica, 66(16): 1889-1897 (2008).
Liao et al, "Evolution of design and development of BACE1 inhibitors", Chinese Journal of Medicinal Chemistry, 16(6): 373-379 (2006).

* cited by examiner

INHIBITORS OF β-SECRETASE

RELATED APPLICATIONS

This application is a 35 U.S.C. §371 national stage filing of International Application No. PCT/US2013/061592, filed Sep. 25, 2013, which claims the benefit of U.S. Provisional Application Ser. No. 61/706,957, filed Sep. 28, 2012, the contents of which are all incorporated herein by reference in their entireties.

FIELD OF THE INVENTION

The present invention relates to spirocyclic indane imidazole 4-amines and their use as inhibitors of the β-secretase enzyme (BACE1) activity, pharmaceutical compositions containing the same, and methods of using the same as therapeutic agents in the treatment of neurodegenerative disorders, disorders characterized by cognitive decline, cognitive impairment, dementia and diseases characterized by production of β-amyloid deposits and/or neurofibrillary tangles.

BACKGROUND OF THE INVENTION

β-Amyloid (also referred to herein as "Abeta" or "Aβ") deposits and neurofibrillary tangles are two major pathologic characterizations associated with Alzheimer's disease (AD). Clinically, AD is characterized by the loss of memory, cognition, reasoning, judgment, and orientation. Also affected, as the disease progresses, are motor, sensory and linguistic abilities until global impairment of multiple cognitive functions occurs. These cognitive losses take place gradually, but typically lead to severe impairment and eventual death in 4-12 years.

β-Amyloid deposits are predominantly an aggregate of Abeta peptide, which in turn is a product of the proteolysis of amyloid precursor protein (APP). More specifically, Aβ peptide results from the cleavage of APP at the C-terminals by one or more γ-secretases, and at the N-terminus by β-secretase enzyme (BACE1), also known as aspartyl protease and memapsin2, as part of the β-amyloidogenic pathway.

BACE activity is correlated directly to the generation of Aβ peptide from APP, and studies increasingly indicate that the inhibition of BACE inhibits the production of Aβ peptide.

Amyloidogenic plaques and vascular amyloid angiopathy also characterize the brains of patients with Trisomy 21 (Down Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders.

Recently, Abeta has been reported to be implicated in the development of retinal ganglion cell (RGC) apotosis in glaucoma, with evidence of caspase-3-mediated abnormal amyloid precursor protein processing, increased expression of Abeta in RGCs in experimental glaucoma and decreased vitreous Aβ levels (consistent with retinal Aβ deposition) in patients with glaucoma. Amyloid deposits have also been associated with macular degeneration in patients suffering from dry age-related macular degeneration (AMD) and in animal models of AMD.

WO2012/087237 discloses spirocyclic indane imidazole 4-amines as inhibitors of beta-secretase.

SUMMARY OF THE INVENTION

The present invention provides compounds that are BACE1 inhibitors and are useful as therapeutic agents in the treatment of a disease or disorder characterized by elevated β-amyloid deposits or β-amyloid levels in a patient. The disclosed compounds have significantly greater potency as inhibitors of BACE1 enzyme activity than the corresponding compounds in WO2012/087237 (see Examples 9 and 10, herein, and Tables 1 and 2 in Example 10).

One embodiment of the invention is a compound represented by a structural formula selected from formulas (I), (Ia), (II) and (IIa):

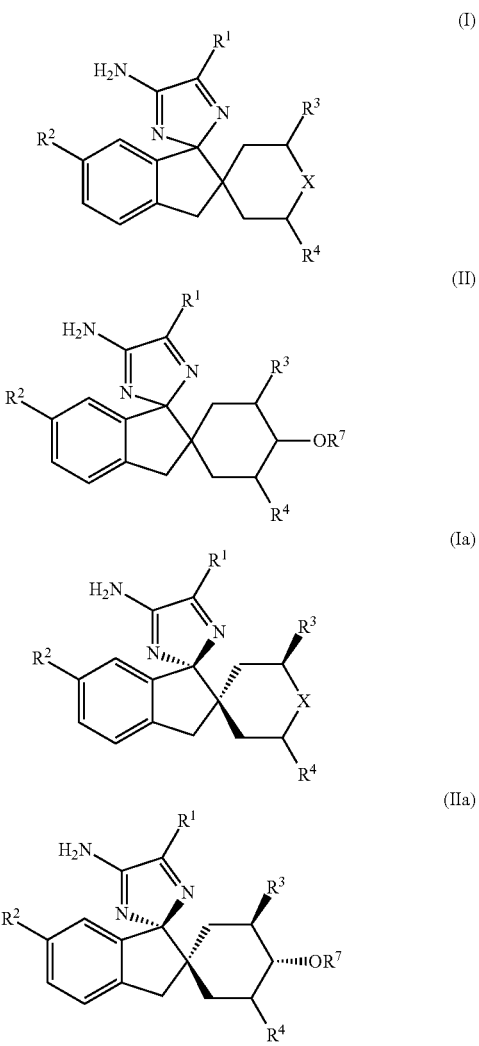

or a pharmaceutically acceptable salt thereof, wherein:

$R^1$ is $C_{1-6}$ alkyl optionally substituted with one or more halogen atoms;

$R^2$ is H, halo, —CN, —OH, aryl, heteroaryl, $C_{1-6}$ alkyl, $C_{2-6}$ alkenyl or $C_{2-6}$ alkynyl, which latter five groups are optionally substituted with one or more groups independently selected from $C_{1-6}$ alkyl, halo, —CN, cycloalkyl, $C_{1-6}$ haloalkyl, —O$C_{1-6}$ alkyl, $C_{2-6}$ alkenyl, $C_{2-6}$ alkynyl and —O$C_{1-6}$ haloalkyl;

—O-aryl, or —O-heteroaryl, each of are optionally substituted with one or more groups independently selected from halogen, —CN and $C_{1-6}$ alkyl; or —NHCO-heteroaryl optionally substituted with one or more groups independently selcted from halo, —CN, —O—$C_{1-6}$ alkyl, $C_{1-6}$ alkyl and $C_{1-6}$ haloalkyl;

$R^3$ and $R^4$ are each independently —H, halo, —CN, —O—$C_{1-6}$ alkyl or $C_{1-6}$ alkyl, wherein the $C_{1-6}$ alkyl group represented by $R^3$ and $R^4$ is optionally substituted with one or more halogen atoms, with the proviso that $R^3$ and $R^4$ cannot both be —H;

X is —O—, —S(O)—, —S(O)$_2$—, —C(O)—, —NR$^a$— or —C(R$^5$R$^6$)—;

$R^a$ is —H or $C_{1-6}$ alkyl;

$R^5$ and $R^6$ are each independently H, halo, —CN, —OR' or $C_{1-6}$ alkyl, wherein the $C_{1-6}$ alkyl group represented by $R^5$ and $R^6$ is optionally substituted with one or more halogen atoms;

$R^7$ is H or $C_{1-6}$ alkyl.

The immediately foregoing compounds are referred to herein as "compounds of the present invention" or simply "compounds of the invention". Another embodiment of the invention is a compound of the present invention or a pharmaceutically acceptable salt thereof for use as a medicament.

Another embodiment of the invention is a pharmaceutical composition comprising a compound of the present invention or a pharmaceutically acceptable salt thereof in admixture with a pharmaceutically acceptable adjuvant, diluent or carrier.

Another embodiment of the invention is a compound of the present invention or a pharmaceutically acceptable salt thereof for use in the treatment of a BACE1 mediated disorder or disease in a subject.

Another embodiment of the invention is the use of a compound of the present invention or a pharmaceutically acceptable salt thereof for the manufacture of a medicament for the treatment of a BACE1 mediated disorder in a subject.

Another embodiment of the invention is a method of treating a subject with a BACE1 mediated disease or disorder, comprising administering to the subject an effective amount of a compound of the present invention or a pharmaceutically acceptable salt thereof.

DETAILED DESCRIPTION OF THE INVENTION

Compounds of the present invention are BACE1 inhibitors represented by Formula (I), (Ia), (II) and (IIa); and the definitions for the variables in Formulas (I), (Ia), (II) and (IIa) are provided above in the Summary of the Invention. Alternatively, for the BACE1 inhibitors represented by Formula (I), (Ia), (II) and (IIa); $R^3$ and $R^4$ are each independently —H or $C_{1-4}$ alkyl, with the proviso that $R^3$ and $R^4$ cannot both be —H; $R^7$ is —H or $C_{1-4}$ alkyl; and the remainder of the variables are as described above in the Summary of the Invention. In another alternative for the BACE1 inhibitors represented by Formula (I), (Ia), (II) and (IIa); $R^3$ and $R^4$ are each independently H, methyl or ethyl, with the proviso that $R^3$ and $R^4$ cannot both be —H; $R^7$ is —H or methyl; and the remainder of the variables are as described above in the Summary of the Invention.

In another embodiment, for the BACE1 inhibitors represented by Formula (I), (Ia), (II) or (IIa), $R^3$, $R^4$ and $R^7$ are as described in the previous paragraph; $R^2$ is -i) CN, halo, phenyl or 6 membered heteroaryl, which two latter groups are optionally substituted with one or more groups selected from halo, —CN, $C_{1-6}$ alkyl, $C_{2-6}$ alkenyl and $C_{2-6}$ alkynyl, or ii) —NHC(O)-(6 membered heteroaryl) optionally substituted with one or more halo groups; and the remainder of the variables are as described above in the Summary of the Invention. Alternatively, for the BACE1 inhibitors represented by Formula (I), (Ia), (II) and (IIa), $R^3$, $R^4$ and $R^7$ are as described in the previous paragraph, $R^2$ is -i) CN, halo, phenyl or pyridyl which latter two groups are optionally substituted with one or more groups selected from halo, —CN, $C_{1-6}$ alkyl, $C_{2-6}$ alkenyl or $C_{2-6}$ alkynyl, or ii) —NHC(O)-pyridyl optionally substituted with one or more halo groups; and the remainder of the variables are as described in the Summary of the Invention. In another alternative for the BACE1 inhibitors represented by Formula (I), (Ia), (II) and (IIa), $R^3$, $R^4$ and $R^7$ are as described in the previous paragraph; $R^2$ is —CN, halo or pyridinyl, the latter group of which is optionally substituted with halo or $C_{2-6}$ alkynyl, or —NHC(O)-pyridyl optionally substituted with halo; and the remainder of the variables are as described in the Summary of the Invention. In yet another alternative for the BACE1 inhibitors represented by Formula (I), (Ia), (II) and (IIa), $R^3$, $R^4$ and $R^7$ are as described in the previous paragraph; $R^2$ is —CN or halo; and the remainder of the variables are as described in the Summary of the Invention.

DEFINITION OF TERMS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

"Alkyl" means a saturated aliphatic branched or straight-chain monovalent hydrocarbon radical having the specified number of carbon atoms. For example, "($C_1$-$C_6$)alkyl" means a radical having from 1-6 carbon atoms in a linear or branched arrangement. "($C_1$-$C_6$)alkyl" includes methyl (—CH$_3$), ethyl (—CH$_2$CH$_3$), propyl (—CH$_2$CH$_2$CH$_3$ and —CH(CH$_3$)CH$_3$), butyl (—CH$_2$CH$_2$CH$_2$CH$_3$, —CH(CH$_3$)CH$_2$CH$_3$, CH$_2$CH(CH$_3$)CH$_3$ and —C(CH$_3$)$_2$CH$_3$), pentyl (—CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)CH$_3$, —C(CH$_3$)$_2$CH$_2$CH$_3$, —CH$_2$C(CH$_3$)$_2$CH$_3$, —CH(CH$_3$)CH(CH$_3$)CH$_3$ and —CH(CH$_2$CH$_3$)CH$_2$CH$_3$), and hexyl (—CH$_2$(CH$_2$)$_4$CH$_3$, —CH(CH$_3$)CH$_2$CH$_2$CH$_2$CH$_3$, —CH$_2$CH(CH$_3$)CH$_2$CH$_2$CH$_3$, —CH$_2$CH$_2$CH(CH$_3$)CH$_2$CH$_3$, —CH$_2$CH$_2$CH$_2$CH(CH$_3$)CH$_3$, —C(CH$_3$)$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH(CH$_3$) CH(CH$_3$)CH$_2$CH$_3$, —CH$_2$CH(CH$_3$)CH(CH$_3$)CH$_3$, —CH(CH$_3$)CH$_2$CH(CH$_3$)CH$_3$, —CH$_2$CH(CH$_2$CH$_3$) CH$_2$CH$_3$, and —CH$_2$CH(CH(CH$_3$)$_2$)CH$_3$).

"Alkenyl" means branched or straight-chain monovalent hydrocarbon radical containing at least one double bond and having specified number of carbon atoms. Alkenyl may be mono or polyunsaturated, and may exist in the E or Z configuration. For example, "($C_2$-$C_6$)alkenyl" means a radical having from 2-6 carbon atoms in a linear or branched arrangement.

"Alkynyl" means branched or straight-chain monovalent hydrocarbon radical containing at least one triple bond and having specified number of carbon atoms. For example, "($C_2$-$C_6$)alkynyl" means a radical having from 2-6 carbon atoms in a linear or branched arrangement.

"Aryl", aryl group", "aryl ring", "aromatic", "aromatic group" and "aromatic ring" are used interchangeably and mean an aromatic monocyclic or polycyclic hydrocarbon ring system. "Aryl" includes, but is not limited to, phenyl, naphthalenyl, fluorenyl, indenyl, azulenyl, and anthracenyl.

"Cycloalkyl" means a saturated aliphatic cyclic hydrocarbon radical having the specified number of carbon atoms. For example, ($C_3$-$C_8$)cycloalkyl means a radical having from 3-8 carbon atoms arranged in a monocyclic ring. A ($C_3$-$C_8$)cycloalkyl includes, but is not limited to, cyclopropyl, cyclobutyl, cyclopentyl, cyclohexyl, cycloheptyl and cyclooctane.

"Heteroaryl" is used interchangeably with "heteroaryl group", "heteroaryl ring", "heteroaromatic", "heteroaromatic group" and "heteroaromatic ring". "The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of an aromatic ring. The term "heteroaryl" is intended to include all the possible isomeric forms.

For example, "heteroaryl" includes, but is not limited to, the following exemplary structures which are not depicted as radicals as each from may be attached through a covalent bond to any atom so long as appropriate valences are maintained:

Monocyclic

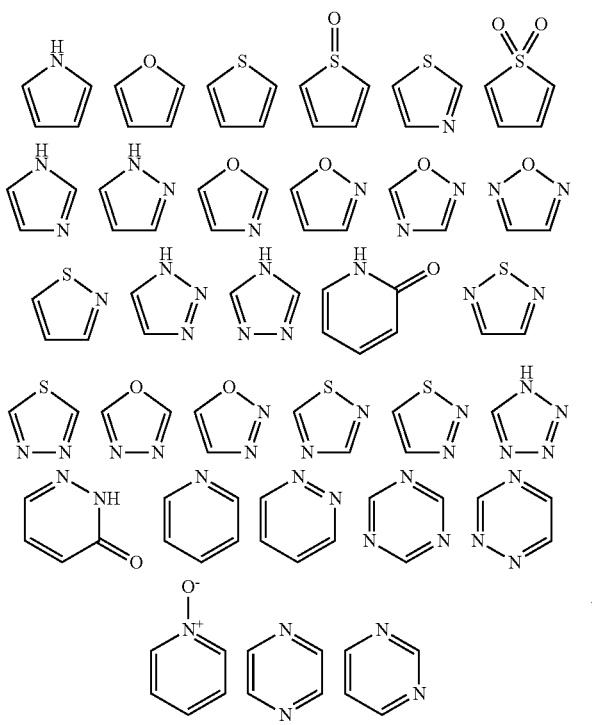

Bicyclic

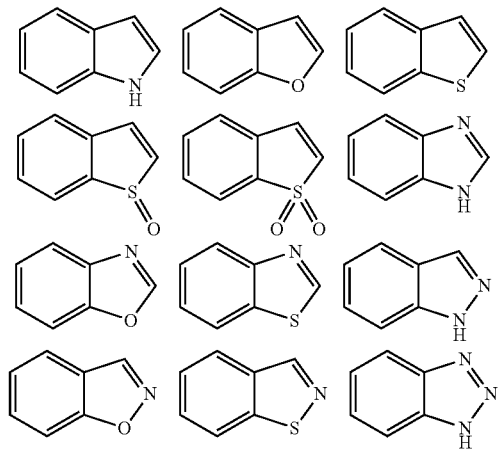

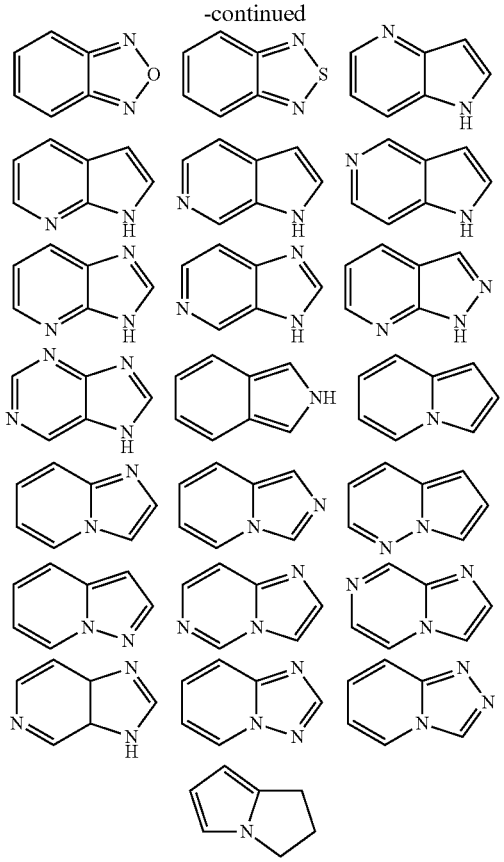

When a compound of the present invention is depicted by name or structure without indicating all tautomeric forms, it is to be understood that the compound and its pharmaceutically acceptable salts shall encompass all tautomers.

When a compound of the present invention is depicted by name or structure without indicating the stereochemistry, it is to be understood that the compound and its pharmaceutically acceptable salts shall encompass all stereo, optical and geometrical isomers (e.g., enantiomers, diastereomers, E/Z isomers, etc.) and racemates thereof, as well as mixtures in different proportions of the separate enantiomers, mixtures of diastereomers, or mixtures of any of the foregoing forms.

When a stereo, optical or geometric isomer is depicted by name or structure, it is to be understood that the stereo, optical and/or geometric isomeric purity of the named or depicted stereo, optical or geometric isomer is at least 60%, 70%, 80%, 90%, 99% or 99.9% pure by weight. Stereo, optical and geometric isomeric purity is determined by dividing the weight of the named or depicted stereo, optical and geometric isomer in a mixture by the total weight of all stereo, optical and geometric isomers in the mixture.

When a compound of the present invention or its pharmaceutically acceptable salt is named or depicted by structure, it is to be understood that solvates, hydrates and the anhydrous form of the compound and solvates, hydrates and anhydrous form of its pharmaceutically acceptable salt are included in the invention. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water. "Anhydrous form" refers to compounds with no solvent or water or substantially no solvent or water incorporated into the crystal structure (e.g., less than 1:10, 1:20; 1:100; or 1:200 molar ratio of solvent or water to compound).

Salts

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Preferred salts are L-mandelic acid and maleic acid. Further pharmaceutically acceptable salts can be formed with cations from metals like aluminium, calcium, lithium, magnesium, potassium, sodium, zinc and the like (see also Pharmaceutical salts, Berge, S. M. et al., J. Pharm. Sci., (1977), 66:1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of acids other than those mentioned above which for example are useful for purifying or isolating the compounds of the present invention (e.g., trifluoro acetate salts) also comprise a part of the invention.

Method of Treatment

The present invention is directed to compounds which are useful in the treatment of disorders or diseases characterized by elevated β-amyloid deposits or β-amyloid levels in a subject wherein the inhibition of the activity of the β-secretase enzyme (BACE1) is of therapeutic benefit, including but not limited to, the treatment, amelioration or prevention of neurodegenerative disorders, disorders characterized by cognitive decline, cognitive impairment, dementia and diseases characterized by production of β-amyloid deposits and/or neurofibrillary tangles.

Compounds of the present invention are useful for treatment of Alzheimer's disease, Trisomy 21 (Down Syndrome), Hereditary Cerebral Hemorrhage with Amyloidosis of the Dutch-type (HCHWA-D), senile dementia, cerebral amyloid angiopathy, degenerative dementia, dementias of mixed vascular and degenerative origin, dementia associated with Parkinson's disease, dementia associated with progressive supranuclear palsy, dementia associated with cortical basal degeneration, diffuse Lewy body type of Alzheimer's disease, dry age related macular degeneration (AMD), and glaucoma. The "dry" form of AMD, also known as "central geographic atrophy", results from atrophy to the retinal pigment epithelial layer below the neurosensory retina, which causes vision loss through loss of photoreceptors (rods and cones) in the central part of the eye. No medical or surgical treatment is currently available for this condition. Treatments available so far (e.g., suggested by the National Eye Institute) include the use of vitamin supplements with high doses of antioxidants, lutein and zeaxanthin, which may slow the progression of dry macular degeneration. Glaucoma is a disease where fluid pressure inside the eye increases, causing irreversible damage to the optic nerve and loss of vision. Abeta colocalizes with apoptotic retinal ganglion cells in experimental glaucoma and induces significant retinal ganglion cell apoptosis in a dose- and time-dependent manner.

Accordingly, the present invention relates to a compound or a pharmaceutically acceptable salt thereof as a medicament.

Furthermore, the present invention relates to the use of a compound in the treatment of a disease and/or condition wherein the inhibition of the activity of the β-secretase enzyme (BACE1) is of therapeutic benefit.

Furthermore, the present invention relates to the use of a compound in the treatment of neurodegenerative disorders, disorders characterized by cognitive decline, cognitive impairment, dementia and diseases characterized by production of β-amyloid deposits or neurofibrillary tangles.

Therefore, the present invention relates to the use of a compound of the present invention in the treatment of Alzheimer's disease, Trisomy 21 (Down Syndrome), Hereditary Cerebral Hemorrhage with Amyloidosis of the Dutch-type (HCHWA-D), senile dementia, cerebral amyloid angiopathy, degenerative dementia, dementias of mixed vascular and degenerative origin, dementia associated with Parkinson's disease, dementia associated with progressive supranuclear palsy, dementia associated with cortical basal degeneration, diffuse Lewy body type of Alzheimer's disease, dry AMD, and glaucoma.

The present invention also provides a method for the treatment of a disorder related to or associated with excessive BACE1 activity in a patient in need thereof which comprises administering to said patient an effective amount of a disclosed compound or a pharmaceutically acceptable salt thereof. The present invention also provides methods for inhibiting the activity of BACE1 in a subject in need thereof, comprising administering to a subject and/or contacting a receptor thereof with an effective amount of at least one disclosed compound or a pharmaceutically acceptable salt thereof. The present invention also provides methods of ameliorating β-amyloid deposits in a subject in need thereof, comprising administering to said subject an effective amount of at least one disclosed compound or a pharmaceutically acceptable salt thereof.

The invention includes a therapeutic method for treating or ameliorating a BACE1 mediated disorder in a subject in need thereof comprising administering to a subject in need thereof an effective amount of a compound of the invention described herein, or pharmaceutically acceptable salts thereof or composition thereof.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be prophylactic (i.e., reducing the likelihood of developing the disorder or disease) or therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome. The compounds taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration.

The dose range of the compounds according to the present invention applicable per day is usually from 0.1 to 3000 mg, preferably from 1 to 2000 mg, more preferably from 10 to 1000 mg, most preferably, 50 or 500 mg. Each dosage unit may conveniently contain from 0.1 to 1000 mg, preferably 25 to 250 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives and powders, etc. The content of the pharmaceutically active compound(s) should be in the range from 0.1 to 95 wt.-%, preferably 5 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

Combination Therapy

In one embodiment, the present invention includes combination therapy for treating or ameliorating a disease or a disorder described herein. The combination therapy comprises administering a combination of at least one compound of the present invention with one or more agent selected from the group of, for example, gamma-secretase inhibitors or modulators; amyloid aggregation inhibitors blocking the formation of Abeta oligomers or Abeta fibrils (e.g., ELND-005); directly or indirectly acting neuroprotective and/or disease-modifying substances; anti-oxidants (e.g., vitamin E or ginkolide); anti-inflammatory substances (e.g., Cox inhibitors, NSAIDs additionally or exclusively having Abeta lowering properties); HMG-CoA reductase inhibitors (statins); acetylcholinesterase inhibitors (e.g., donepezil, rivastigmine, tacrine, or galantamine); NMDA receptor antagonists (e.g., memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunization with Abeta or parts thereof or passive immunization with humanized anti-Abeta antibodies or nanobodies) for the treatment of the above-mentioned diseases and conditions.

Combination therapy includes co-administration of the compound of the invention with one or more other agent, sequential administration of the compound and one or more other agent, administration of a composition containing a compound and one or more other agent, or simultaneous administration of separate compositions containing the compound and one or more other agent.

EXPERIMENTAL SECTION

Methods of Preparation of Compounds

Compounds of the invention can be prepared employing conventional methods that utilize readily available reagents and starting materials. The reagents used in the preparation of the intermediates of this invention can be either commercially obtained or can be prepared by standard procedures described in the literature.

Microwave reactions were carried out in CEM reactor using discovery SP system. Where NMR data are presented, spectra were obtained in Varian-400 (400 MHz). Spectra are reported as ppm downfield from tetramethylsilane with number of proton, multiplicities and, in certain instances, coupling constants indicated parenthetically along with reference to deuterated solvent. Compounds were purified by basic preparative HPLC method as described below.

Method 1:

Mobile phase A: water with 0.05% $NH_4OH$; Mobile phase B: ACN; Flow rate: 25 mL/min; Detection: UV 220 nm/254 nm; Column: Phenomenex Gemini C18 250*30 mm*5 um; Column temperature: 30° C.

| Time in min | % A | % B |
|---|---|---|
| 0.0 | 68 | 32 |
| 12.00 | 38 | 62 |
| 12.20 | 0 | 100 |
| 13.5 | 0 | 100 |
| 13.7 | 90 | 10 |

Method 2:

Mobile phase A: water with 0.05% $NH_4OH$; Mobile phase B: ACN; Flow rate: 25 mL/min; Detection: UV 220 nm/254 nm; Column: Durashell C18 250*30 mm*5 um; Column temperature: 30° C.

| Time in min | % A | % B |
|---|---|---|
| 0.0 | 67 | 33 |
| 12.00 | 47 | 53 |
| 12.20 | 0 | 100 |
| 13.5 | 0 | 100 |
| 13.7 | 90 | 10 |

LC-MS data were obtained by utilizing the following chromatographic conditions:

Method 1:

HPLC System: Waters ACQUITY; Column: Waters ACQUITY CSH C18 1.7 μM.

Guard column: Waters Assy. Frit, 0.2 μM, 2.1 mm; Column tem: 40° C.

Mobile Phase: A: TFA: Water (1:1000, v:v) Mobile phase B: TFA: ACN (1:1000, v:v); Flow Rate: 0.65 mL/min; Injection Volume: 2 μL; Acquisition time: approximately 1.5 minute.

Gradient Program:

| Time (min) | B % |
|---|---|
| 0 | 10 |
| 0.8 | 90 |
| 1.20 | 90 |
| 1.21 | 10 |

Mass Spectrometer Parameters

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v.

Source Temperature: 120° C.; Desolvation Temperature: 500° C.; Desolvation Gas Flow: Nitrogen Setting 650 (L/h); Cone Gas Flow: Nitrogen Setting 50 (L/h).

Racemic compounds were separated by chiral column using supercritical fluid technology by methods described below.

Method A:

Instrument: Thar SFC 80; Column: AD 250 mm*30 mm, 5 μm; Mobile phase: A: Supercritical $CO_2$, B: IPA (0.05% DEA), A: B=80:20 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.

Method B:

Instrument: SFC MG2; Column: OJ 250 mm*30 mm, 5 μm; Mobile phase: A: Supercritical $CO_2$, B: MeOH (0.05% DEA), A:B=90:10 at 70 ml/min; Column Temp: 38° C.; Nozzle Pressure: 100 Bar Nozzle Temp: 60° C.; Evaporator Temp: 20° C.; Trimmer Temp: 25° C.; Wavelength: 220 nm.

The invention is illustrated by the following examples, in which the following abbreviations may be employed:

| Abbreviation | Meaning |
|---|---|
| ACN | acetonitirle |
| Boc | tert-butoxy carbonyl or t-butoxy carbonyl |
| $Boc_2O$ | di-tert-butyl-dicarbonate |
| brine | saturated aqueous nacl |
| DCM | methylene chloride |
| DMA | dimethyl acetamide |
| DMF | dimethyl formamide |
| dppf | 1,1-bis(diphenylphosphino)ferrocene |
| Et | ethyl |
| EtI | ethyl iodide |
| $Et_3N$ | triethylamine |
| EtOAc | ethyl acetate |
| EtOH | ethanol |
| H | hour(s) |
| HPLC | high performance liquid chromatography |
| min | minute(s) |
| MeOH | methanol |
| Me | methyl |
| mL | milliliters |
| mmol | millimoles |
| mg | milligram |
| NaOMe | sodium methoxide |
| $PdCl_2$dppf | [1,1-bis(diphenylphosphino)ferrocene] dichloropalladium(ii) |
| Rt | room temperature |
| SFC | super critical fluid chromatography |
| t-BuOK | potassium tert butoxide |
| $t-BuNH_2$—$BH_3$ | tert butylamine-borane complex |
| t-BuOOH | tert butyl peroxide |
| TEA | triethylamine |
| TFA | trifluoroacetic acid |
| THF | tetrahydrofuran |
| TLC | thin layer chromatography |
| $Ti(OEt)_4$ | titanium tetraethoxide |
| V | volume |
| XPhos | dicyclohexyphosphino-2',4',6'-triisopropyl-1,1'-biphenyl |

Example 1

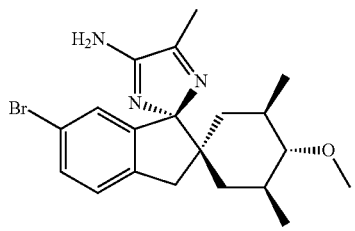 [SMILES: CO[C@H]1[C@H](C)C[C@@]2(Cc3ccc(Br)cc3[C@@]23N=C(C)C(N)=N3)C[C@@H]1C]

Step 1: Synthesis of Intermediate 3

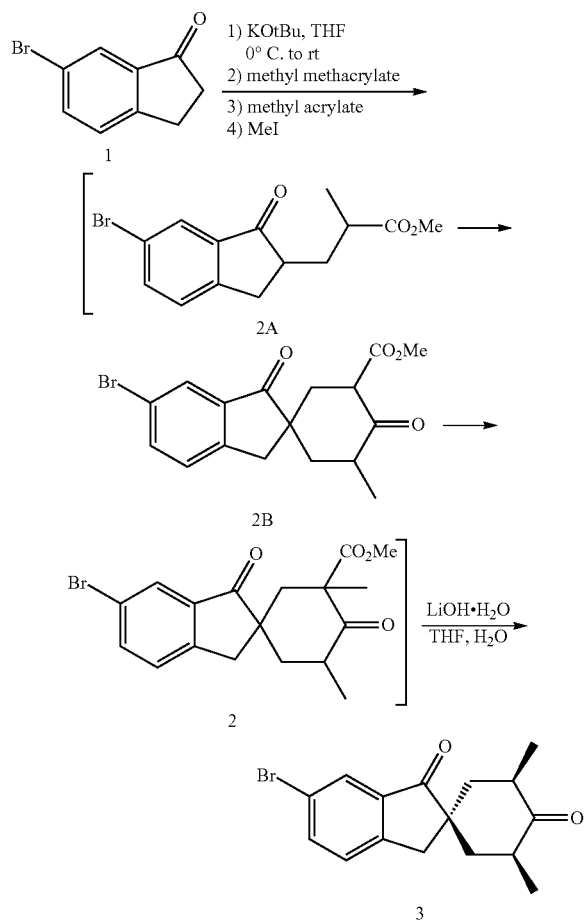

To a mixture of 6-bromo-indan-1-one (100.00 g, 473.8 mmol) in anhydrous THF (1 L) at 0° C. was added t-BuOK (58.5 g, 521.2 mmol). After 5 minutes, the mixture was warmed to rt and stirred for another 10 min. Methyl methacrylate (49.8 g, 53.2 mL, 497.5 mmol, 1.05 eq) was added in one portion. After 2 h, methyl acrylate (49.0 g, 51.2 mL, 568.6 mmol, 1.2 eq) was added to the reaction mixture. After 3 h of stirring at rt, MeI (101 g, 44.3 mL, 710.7 mmol, 1.5 eq) was added to the reaction mixture, and the mixture was further stirred for 16 h. H₂O (1 L) was added followed by LiOH*H₂O (79.5 g, 1895 mmol, 4.0 eq). The mixture was stirred for 28 h at rt. THF was removed under reduced pressure. The residue was diluted with H₂O (1 L), filtered, and washed with H₂O until the filtrate was neutral. The product was washed with MeOH to afford 50 g of intermediate 3.

Step 2: Synthesis of Intermediate 4

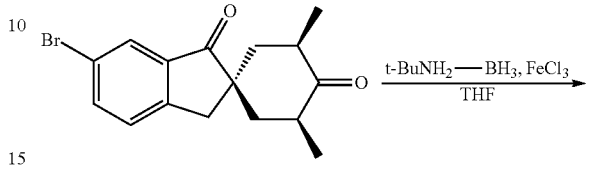

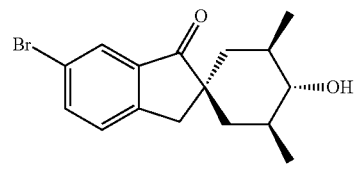

A mixture of FeCl$_3$ (6.0 g, 37.0 mmol) and toluene (60 mL) was cooled to 0° C. A mixture of intermediate 3 (11.9 g, 37.0 mmol) in THF (48 mL) was added to the mixture. The mixture was stirred for 5 min at 0° C. and then cooled to −10° C. A solution of t-BuNH$_2$—BH$_3$ (3.5 g, 40.7 mmol) in THF (12 mL) was added dropwise to the reaction mixture at −10° C. The reaction mixture was stirred at about −10° C. for 30 min, quenched with aqueous HCl solution (6N, 10 mL), stirred at about 0° C. for 30 min, and then allowed to warm to rt. The mixture was concentrated to remove THF, and toluene (60 mL) was added. The aqueous layer was removed, and the organic phase was washed with water (3×60 mL). The organic phase was concentrated to half volume, heated to 50° C. to obtain a solution, and then cooled to 0° C. over 1 h and held at 0° C. for 1 h. The solid was filtered and washed with cold (0° C.) toluene (12 mL), and dried under vacuum to give compound 4 (9.93 g).

LC-MS (method 1): tR=1.24 min, MS (ESI) m/z 323.1 [M+H]$^+$.

$^1$H-NMR (CDCl$_3$): δ: 7.88-7.89 (s, 1H), 7.67-7.69 (d, 1H), 7.31-7.33 (d, 1H), 3.60 (s, 1H), 2.98 (s, 2H), 1.76-1.79 (m, 4H), 1.07-1.08 (m, 2H), 1.02-1.06 (m, 6H).

Step 3: Synthesis of Intermediate 5

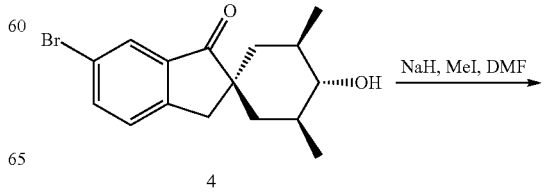

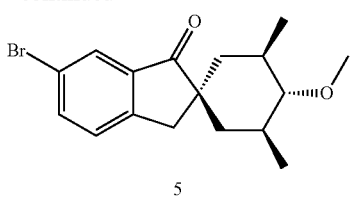

5

To a mixture of intermediate 4 (20.0 g, 61.9 mmol) in DMF (200 mL) was added NaH (5.0 g, 123.8 mmol) at 0° C. and the mixture was stirred for 15 min at 0° C. MeI (17.6 g, 123.8 mmol) was added at 0° C. and the mixture was warmed to rt and stirred for 1.5 h at rt. The mixture was quenched with H₂O and extracted with EtOAc. The combined organic phase was washed with H₂O followed by brine, dried and concentrated to afford crude product, which was purified by column on silica gel (petroleum ether: ethyl acetate; 30:1 to 5:1) to afford intermediate 5 (20 g).

Step 4: Synthesis of Intermediate 6

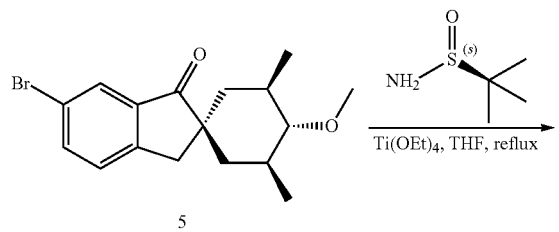

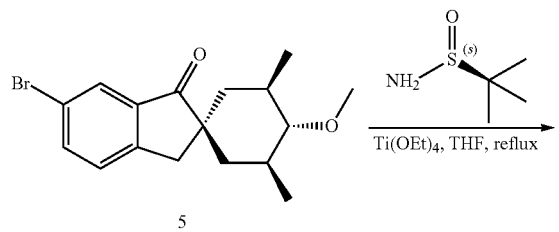

A mixture of intermediate 5 (20.0 g, 59.3 mmol) and titanium (IV) ethoxide (108.2 g, 474.4 mmol) in dry THF (200 ml) was stirred at rt for 1 h. (S)—N-tert-butylsulfinamide (29 g, 237.2 mmol) was added and the resulting mixture was stirred at 80° C. under N₂ atmosphere overnight. The reaction mixture was cooled and H₂O (400 ml) was added. The mixture was filtered and the aqueous layer was extracted with EtOAc (3×400 mL). The combined organic phase was dried and concentrated under reduced pressure to give crude intermediate. This was purified by column chromatography on silica gel (petroleum ether: ethyl acetate; 20:1) to yield intermediate 6 (18.4 g).

Step 5: Synthesis of Intermediate 7

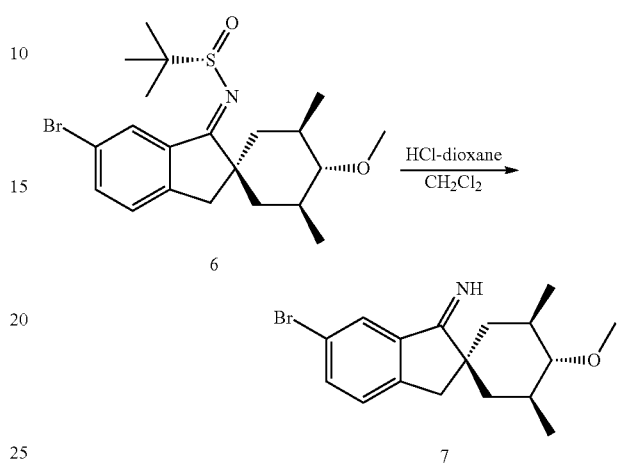

To a solution of intermediate 6 (1.0 g, 2.3 mmol) in anhydrous DCM (10 mL), HCl in dioxane (4 M, 2 mL, 8.0 mmol) was added at 0° C. with stirring and stirred at 0° C. for 1 h. The mixture was quenched by addition of NaHCO3 (20 mL) with stirring for about 5 min, then was extracted with DCM (3×20 mL). The combined organic layer was washed with brine (2×20 mL), dried, filtered and the solvent was removed under reduced pressure to give the crude intermediate 7 (800 mg) which was used directly in next step without purification.

LCMS: $t_R$=2.10 min, MS (ESI) m/z 336.1 [M+H]⁺.

Step 6: Synthesis of Intermediate 8

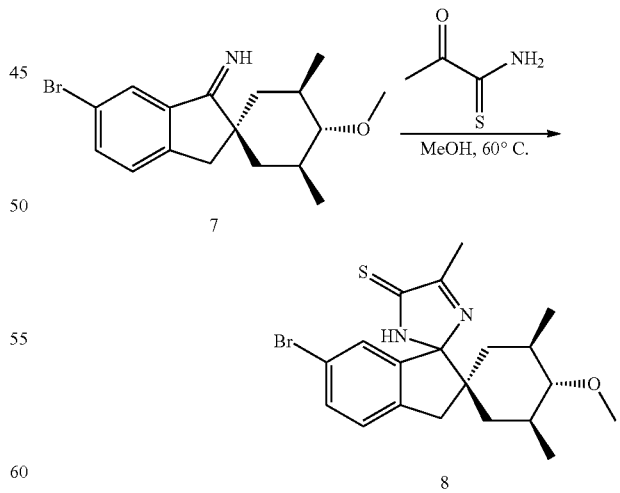

2-oxopropanethioamide (370 mg, 3.6 mmol), was added to a mixture of intermediate 7 (800 mg, 2.4 mmol) in MeOH (15 mL, anhydrous) and the resulting mixture was stirred at 60° C. overnight. After cooling to rt, the resulting precipitate was collected by filtration and was washed with cold MeOH (2×5 mL). The solid was dried under vacuum to give crude intermediate 8 (600 mg), which was used directly in next step without purification.

LCMS: $t_R$=1.19 min, MS (ESI) ink 420.9 [M+H]$^+$.

Step 7: Synthesis of Example 1

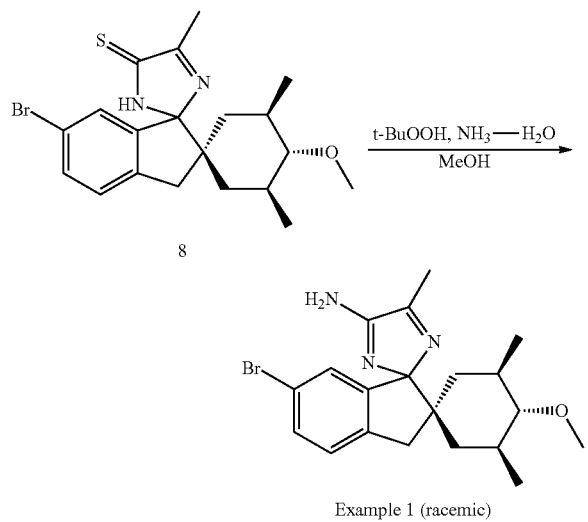

Intermediate 8 (600 mg, 1.4 mmol) was added to a mixture of MeOH (20 mL) and THF (10 mL). A solution of t-BuOOH (5 mL, 36 mmol, 65% in H$_2$O) and NH$_4$OH (5 mL), were added and the resulting mixture was stirred overnight at rt. Water (10 mL) and brine (10 mL) were added, the mixture was extracted with EtOAc (3×30 mL), the combined organic layer was washed with brine (2×20 mL), dried, filtered and concentrated. The resulting residue was purified by preparative HPLC (method 1) to give racemic mixture of Example 1 (300 mg). The racemic mixture was further purified by SFC chiral chromatography method A to yield the desired Example 1 as first eluting isomer.

LCMS: $t_R$=1.01 min; MS (ESI) m/z 404.1 [M+H]$^+$.

$^1$H NMR (CD3OD): δ 7.38-7.42 (dd, J=7.6, 1.6 Hz, 1H), 7.26-7.28 (d, J=7.6 Hz, 1H), 6.85-6.86 (d, J=1.6 Hz, 1H), 3.43 (s, 3H), 3.06-3.18 (m, 2H), 2.28-2.36 (m, 4H), 1.62-1.78 (m, 2H), 1.45-1.60 (m, 2H), 1.15-1.25 (m, 1H), 0.90-1.10 (m, 6H), 0.81-0.87 (m, 1H).

SFC (method 1): $t_R$=4.19 min.

Example 2

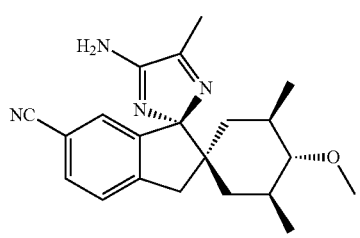 [SMILES: CO[C@H]1[C@H](C)C[C@@]2(Cc3ccc(C#N)cc3[C@@]23N=C(C)C(N)=N3)C[C@@H]1C]

Step 1: Synthesis of Intermediate 10

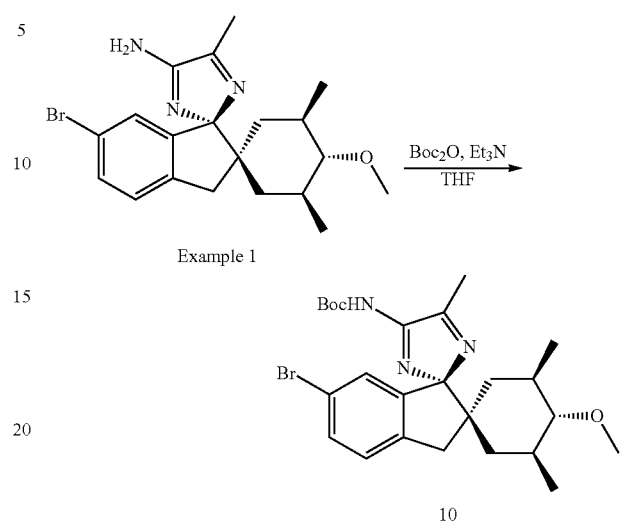

To a mixture of Example 1 (300 mg, 0.74 mmol) in THF (10 mL), Boc$_2$O (480 mg, 2.2 mmol) and TEA (300 mg, 3.0 mmol) were added and stirred overnight at rt. The mixture was concentrated and the resulting residue was purified by column chromatography on silica gel (petroleum ether: ethyl acetate; 10:1 to 1:1) to give intermediate 10 (350 mg).

LCMS: $t_R$=0.90 min, MS (ESI) m/z 404.1 [M+H]$^+$.

$^1$H NMR: (CDCl$_3$), δ 9.82 (s, 1H), 7.41-7.44 (d, J=8.0 Hz, 1H), 7.18-7.20 (d, J=7.6 Hz, 1H), 6.99 (s, 1H), 3.43 (s, 3H), 3.08 (s, 2H) 2.24-2.36 (m, 4H), 1.47-1.72 (m, 14H), 0.81-1.05 (m, 7H).

Step 2: Synthesis of Example 2

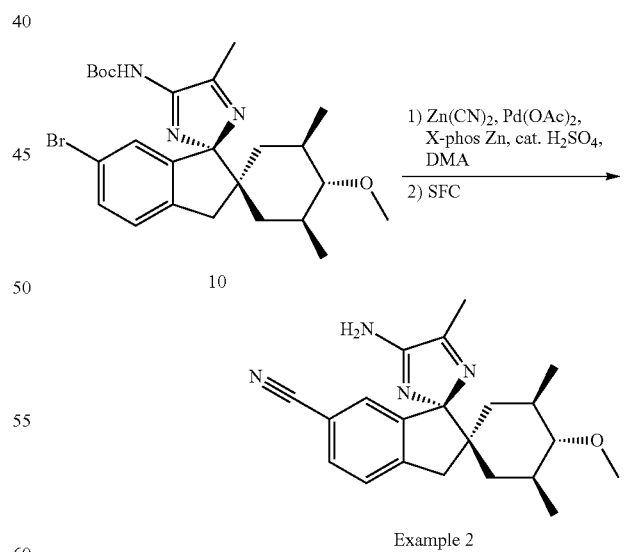

Concentrated sulfuric acid (48 μL) was added to DMA (20 mL) and the solvent was purged with N$_2$ for 20 min. In a separate flask, Pd(OAc)$_2$ (0.3 g) and Xphos (1.25 g) were added under N$_2$, followed by the above mentioned solvent. The resulting mixture was then heated at 80° C. for 30 min to give mixture A.

In an another flask, DMA (50 mL) was purged with $N_2$ and intermediate 8 (2.2 g, 4.0 mmol), $Zn(CN)_2$ (0.5 g, 4.0 mmol) and zinc dust (14.1 mg) were added. The mixture A was added to this solution, and the resulting mixture was heated at 90° C. for 1 h. The reaction mixture was cooled to room temperature, diluted with $H_2O$ (100 mL) and EtOAc (100 mL) and stirred for 10 minutes. The mixture was filtered through celite, and the organic layer was separated. The aqueous layer was then extracted with EtOAc (2×30 mL). The combined organic layer was washed with water, brine and dried and the solvent was removed under reduced pressure. The crude product was first purified by preparative HPLC (method 2) followed by SFC method A to give Example 2 (9.4 mg).

LCMS: $t_R$=0.88 min, MS (ESI) m/z 351.2 [M+H]$^+$.

$^1$H NMR: (Methanol-d4): δ 7.62-7.65 (dd, J=1.2, 7.6 Hz, 1H), 7.52-7.55 (d, J=8.0 Hz, 1H), 7.09 (s, 1H), 3.43 (s, 3H), 3.26-3.31 (d, J=16.4 Hz, 1H), 3.18-3.23 (d, J=16.0 Hz, 1H), 2.29-3.35 (m, 4H), 1.60-1.75 (m, 2H), 1.45-1.55 (m, 2H), 1.18-1.27 (m, 1H), 0.96-0.98 (d, J=4.0 Hz, 3H), 0.94-0.96 (d, J=4.0 Hz, 3H), 0.82-0.90 (m, 1H).

Example 3

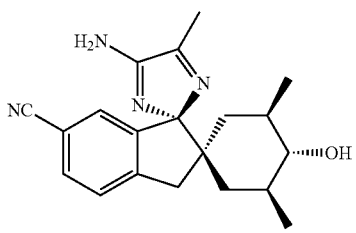

Example 3 was synthesized from intermediate 4 by the method described in step 6 through step 11 of Example 1 followed by methods described in step 1 and 2 of Example 2. The final racemic crude product was purified by chiral SFC method B to yield Example 3 as first eluting isomer.

LCMS: $t_R$=0.41 min, MS (ESI) m/z 337.1 [M+H]$^+$.

$^1$H NMR: (Methanol-d4), δ 7.62-7.65 (dd, J=7.6, 1.2 Hz, 1H), 7.51-7.54 (d, J=7.6 Hz, 1H), 7.11 (s, 1H), 3.26-3.31 (m, 1H), 3.18-3.23 (d, J=16.4 Hz, 1H), 2.46-2.52 (t, J=9.6 Hz, 1H), 2.32 (s, 3H), 1.45-1.60 (m, 4H), 1.14-1.21 (t, J=13.2 Hz, 1H), 0.95-0.96 (d, J=2.8 Hz, 3H), 0.93-0.95 (d, J=3.2 Hz, 3H), 0.81-0.88 (t, J=12.8 Hz, 1H).

Example 4

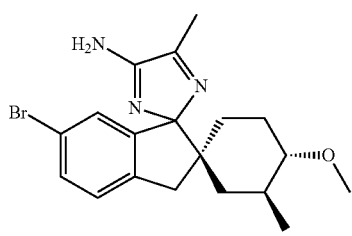 [SMILES: CO[C@H]1CC[C@@]2(Cc3ccc(Br)cc3C23N=C(C)C(N)=N3)C[C@@H]1C]

Step 1: Synthesis of Intermediate 13

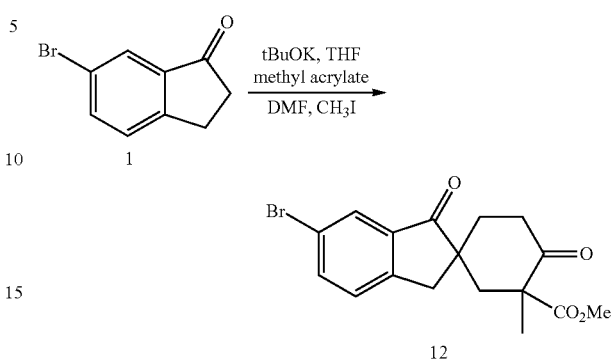

An oven dried 3 L flask was charged with 6-bromo-1-indanone (100 g, 473.8 mmol), methyl acrylate (86.4 g, 90 mL, 995 mmol, 2.1 eq), anhydrous THF (800 mL) and cooled to 0° C. A small portion of tBuOK (0.5 g) was added, and after 2 min, another small portion of tBuOK (0.5 g) was added. After 5 min., the cooling bath was removed and remaining tBuOK (63 g) was added in even portions over 20 minutes (64 g, 568.6 mmol). The mixture was stirred for another 2 h at room temperature. DMF (240 mL) was added to the reaction mixture, followed by MeI (60 mL, 947.6 mmol) and the mixture was stirred for another 12 h. The reaction was quenched with 10% citric acid solution and concentrated under reduced pressure to remove most of organic solvent before it was filtered. The cake was washed with water, followed by MeOH to give the crude intermediate 12 (200 g) which was used to next step directly.

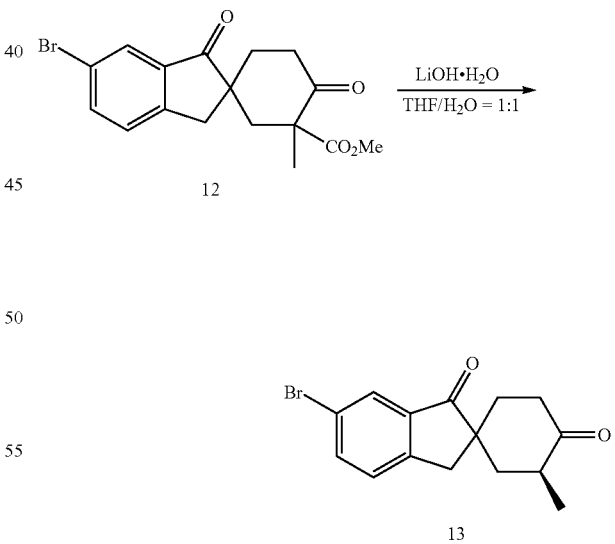

Intermediate 12 (200 g, 547.6 mmol, crude) was added to mixture of THF and $H_2O$ (1:1; 3.6 L) followed by LiOH.H2O (92 g, 2190 mmol). The mixture was stirred for 16 h at rt and then 12 h at 70° C. The reaction mixture was concentrated under reduced procedure to remove THF and filtered. The cake was washed with $H_2O$, and then it was stirred with MeOH (50 mL) for a five minutes and filtered again, and washed with additional amounts of cold MeOH (50 mL). The solid was collected to afford intermediate 13 (75 g).

Step 2: Synthesis of Intermediate 14

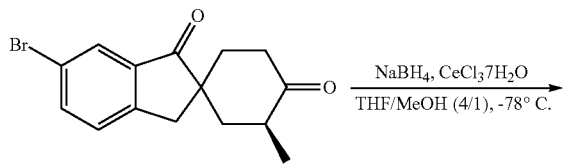

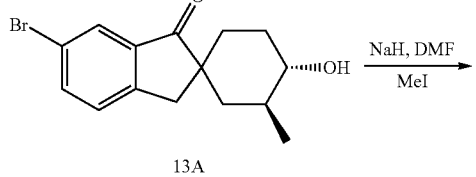

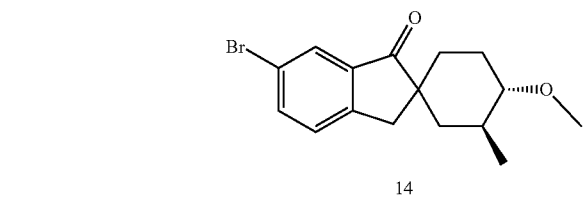

A dry flask was charged with CeCl$_3$.7H$_2$O (1.2 g, 3.3 mmol) and anhydrous MeOH (60 mL) under a N$_2$ atmosphere and stirred to yield clear solution. Compound 13 (10.0 g, 32.6 mmol) and anhydrous THF (240 mL) were added under N$_2$ atmosphere, the mixture was cooled down to −78° C. NaBH$_4$ (0.4 g, 13.0 mmol) was added at −78° C. under a N$_2$ atmosphere with vigorous stirring. The mixture was stirred at −78° C. for 20 min. The reaction was quenched by addition of saturated aqueous NH$_4$Cl (100 mL) and H$_2$O (200 mL) at −78° C. with stirring. The mixture was slowly allowed to warm to ambient temperature. The mixture was extracted with ethyl acetate (3×150 mL). The combined organic layer was washed with H$_2$O (2×200 mL), brine (2×200 mL), dried, filtered and concentrated under vacuum, the residue was purified by column chromatography on silica gel (petroleum ether: ethyl acetate; 20:1 to 3:1) to give intermediate 13A (7.5 g).

LC-Ms: $t_R$=3.19 min: MS (ESI) m/z 311.0 [M+H]$^+$.

$^1$H NMR: (CDCl$_3$): δ 7.59 (s, 1H), 7.22-7.25 (d, J=8.4 Hz, 1H), 7.08 (s, 1H), 6.88-6.91 (dd, J=2.4, 8.4 Hz, 1H), 6.80-6.81 (d, J=2.4 Hz, 1H), 5.84 (s, 1H), 4.87 (s, 2H), 4.31-4.36 (m, 2H), 3.50-3.55 (q, J=6.8 Hz, 2H), 3.15-3.25 (m, 1H), 3.09-3.14 (d, J=15.6 Hz, 1H), 3.00-3.06 (d, J=15.2 Hz, 1H), 1.90-2.10 (m, 3H), 1.25-1.50 (m, 5H), 1.15-1.25 (t, J=6.4 Hz, 3H).

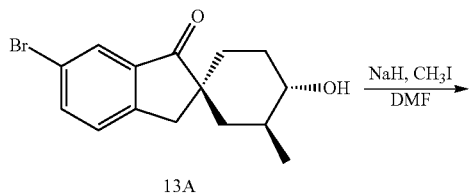

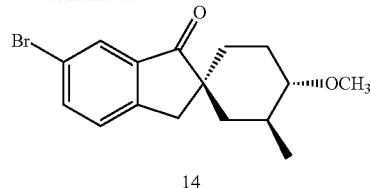

NaH was added to a mixture of intermediate 13A (6.18 g, 20 mmol) in DMF (20 mL) (0.96 g, 40 mmol) at 0° C. and stirred at 0° C. for 2 h, then MeI (3.5 mL) was added to the mixture and stirred overnight. The mixture was diluted with EtOAc (40 mL) and H$_2$O (40 mL). The organic layer was separated and the aqueous layer was extracted with EtOAc (2×60 mL). The combined organic phases were dried and the solvent was removed to give intermediate 14 (5.0 g).

Step 3: Synthesis of Intermediate 15A & 15B

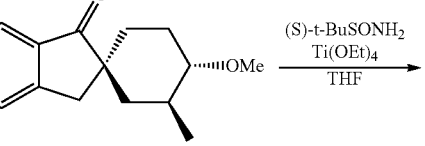

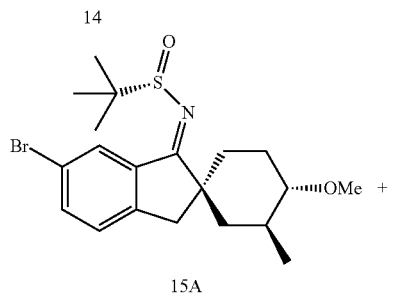

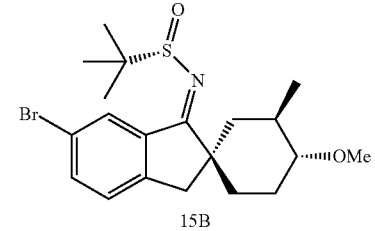

To a mixture of intermediate 14 (5.0 g, 15.3 mmol) in THF (100 mL) was added Ti(OEt)$_4$ (35.0 g, 153 mmol) and stirred at room temperature for 1 h. (S)N-tert-butylsulfinamide (7.4 g, 61.2 mmol) was added and refluxed overnight. The solution was cooled to room temperature and the mixture was partitioned between H$_2$O (80 mL) and EtOAc (80 mL). The aqueous layer was extracted with EtOAc (3×80 mL). The combined organic layers were washed with brine (50 mL), dried and concentrated to the residue. The residue was purified by column chromatography on silica gel (petroleum ether: EtOAc; 20:1) to yield intermediate 15A (1.6 g) and 15B (1.4 g) respectively.

Example 4 was synthesized from intermediate 15A by the method described in step 4 though step 6 in Example 1.

LC-Ms: $t_R$=3.19 min: MS (ESI) m/z 390.23 [M+H]$^+$.

Example 5

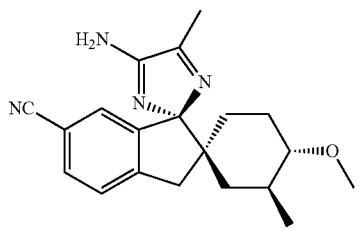 [SMILES: CO[C@H]1CC[C@@]2(Cc3ccc(C#N)cc3[C@@]23N=C(C)C(N)=N3)C[C@@H]1C]

Example 5 was synthesized from Example 4 by the method described in Example 2.

LC-Ms: $t_R$=2.99 min: MS (ESI) m/z 337.23 [M+H]$^+$.

$^1$HNMR: (CD$_3$OD): δ 7.60-7.62 (dd, J=7.6, 1.2 Hz 1H), 7.50-7.52 (d, J=7.6 Hz 1H), 7.07 (s, 1H), 3.33 (s, 3H), 3.25-3.33 (m, 1H), 3.15-3.20 (d, J=16.4 Hz 1H), 2.61 (m, 1H), 2.31 (s, 1H), 2.04-2.10 (m, 1H), 1.43-1.58 (m, 4H), 1.28-1.31 (m, 1H), 0.91-0.93 (d, J=6.4 Hz 3H), 0.78-0.86 (t, J=12.8 Hz, 1H).

Example 6

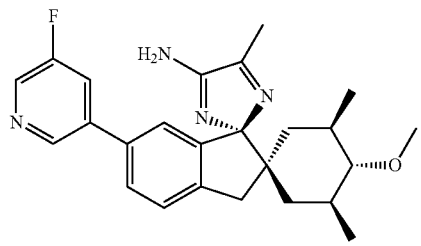 [SMILES: CO[C@H]1[C@H](C)C[C@@]2(Cc3ccc(-c4cncc(F)c4)cc3[C@@]23N=C(C)C(N)=N3)C[C@@H]1C]

3-Fluoro-5-pyridine boronic acid (90 mg, 0.66 mmol) was added to a solution of Example 1 (350 mg, 0.6 mmol) in dioxane (5 mL) followed by aqueous Cs$_2$CO$_3$ solution (2 mL, 2 M in water). The mixture was purged by bubbling a steam of N$_2$ for 5 min, then Pd(dppf)Cl$_2$ (40 mg, 0.06 mmol) was added. The final mixture was stirred for 2 h at 110° C. under a N$_2$ atmosphere. The reaction was cooled to rt, diluted with EtOAc and filtered. The filtrate was concentrated and purified by SFC method A to yield Example 6.

LCMS: $t_R$=0.99 min, MS (ESI) m/z 421.2 [M+H]$^+$.

$^1$H NMR (CD3OD): δ 8.57-8.59 (t, J=1.2 Hz, 1H), 8.39-8.40 (d, J=2.0 Hz, 1H), 7.80-7.85 (m, 1H), 7.58-7.61 (dd, J=7.6, 1.6 Hz, 1H), 7.47-7.50 (d, J=7.6 Hz, 1H), 7.02 (s, 1H), 3.42 (s, 3H), 3.13-3.26 (m, 2H), 2.25-2.38 (m, 4H), 1.62-1.69 (m, 2H), 1.51-1.61 (m, 2H), 1.21-1.31 (m, 1H), 0.94-0.97 (m, 6H), 0.83-0.90 (m, 1H).

$^{19}$F NMR: (CD3OD): δ −128.59 ppm.

Example 7

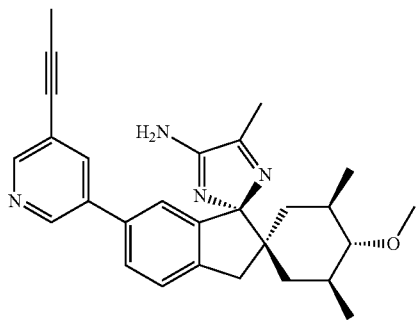 [SMILES: CC#Cc1cncc(-c2ccc3c(c2)[C@@]2(N=C(C)C(N)=N2)[C@@]2(C3)C[C@@H](C)[C@H](OC)[C@@H](C)C2)c1]

Example 7 was synthesized by the method described in Example 6 utilizing (5-(prop-1-yn-1-yl) pyridin-3-yl) boronic acid in lieu of 3-Fluoro-5-pyridinyl boronic acid LCMS: $t_R$=1.01 min, MS (ESI) m/z 441.2 [M+H]$^+$.

$^1$H NMR: (CD$_3$OD): δ 8.61 (d, J=2.0 Hz, 1H), 8.46 (d, J=1.6 Hz, 1H), 7.96 (d, J=2.0 Hz, 1H), 7.55-7.59 (m, 1H), 7.48-7.50 (m, 1H), 6.99 (d, J=1.6 Hz, 1H), 3.45 (s, 3H), 3.16-3.28 (m, 2H), 2.30-2.37 (m, 4H), 2.10 (s, 3H), 1.66-1.80 (m, 2H), 1.52-1.65 (m, 2H), 1.23-1.30 (m, 1H), 0.96-0.99 (m, 6H), 0.85-0.91 (t, J=12.8 Hz, 1H).

Example 8

The following compounds can be synthesized by suitable modification of the procedures described in Examples 1-7, for example, by a suitable selection of starting materials.

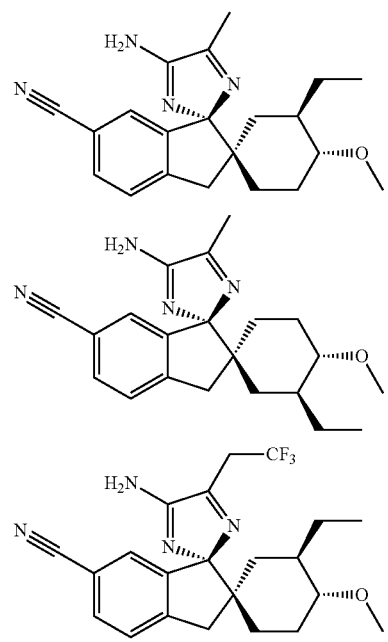

-continued

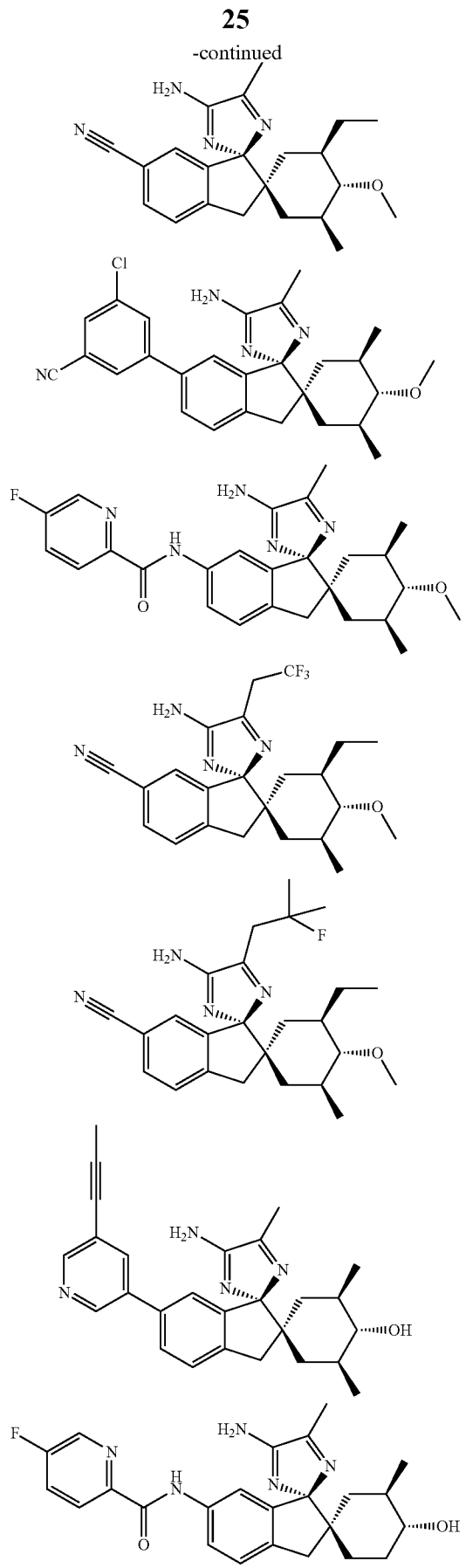

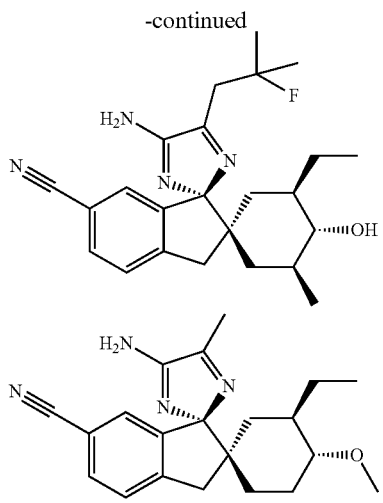

Example 9

BACE1 Assay (Assay 1)

The inhibitory activity of compounds was assessed by a fluorescence quench assay of BACE1 activity using commercially available substrate HiLyte Fluor™488-Glu-Val-Asn-Leu-Asp-Ala-Glu-Phe-Lys-(QXL™ 520)-OH (SEQ ID NO:1) (AnaSpec, San Jose, Calif.) and truncated human beta-secretase, BACE1 (amino acids 1-454) fused to a myc-his tag and secreted from HEK293/BACE$_{ect.}$ cells into OptiMEM™ (Invitrogen). The substrate was dissolved at 1 mg/ml in DMSO.

The assay was performed in the presence of OptiMEM™ (supernatant collected over 24 h and cleared from cellular debris by centrifugation) containing the ectodomain of BACE1, 25 µl water containing the desired 2-fold concentration of test compound and 2% DMSO, 1 µM substrate peptide, 20 mM NaOAc, pH 4.4, and 0.04% Triton-X100 in a total assay volume of 50 µl in a 384 well plate. In general, 25 µl of compound dilution were added to the plate followed by the addition of 10 µl of BACE1 containing OptiMEM™ diluted 1:10 in water with 0.2% Triton X-100. The reaction was started with the addition of 15 µl substrate in NaOAc buffer. The reaction was incubated at rt (dark) in an Envision® multilabel reader (Perkin Elmer) and the cleavage of the substrate was recorded as kinetic for 60 min at ex: 485 nm, em: 538 nm. Blank wells containing no enzyme were included on each plate.

The intensity of fluorescence was regressed against time in order to derive velocities of reaction in all 384 wells. These velocities were used for calculating percent control using an uninhibited control containing 1% DMSO as 100% and a blank control performed in the absence of enzyme as 0%. IC$_{50}$ values were calculated by fitting percent control vs. test compound concentration using Assay Explorer®.

Example 10

H4-APPwt Cell-Based Assay (Assay 2)

Cellular potency of the compounds was assessed in an assay monitoring production of Abeta1-x peptides in the H4 neuroglioma cell line (ATCC, Cat. #HTB-148) stably expressing human APP. Tested compounds were dissolved in DMSO and pre-diluted in the culture medium (DMEM containing 10% FBS and 1% penicillin/streptomycin) to achieve twice the final concentration of the compounds in the assay. Equal volumes of the 2× solutions of the tested compounds and cell suspension were added to a 96-well culture plate, so that each well contained ~10,000 cells in a final volume of 200 µl. Final concentration of DMSO in the assay was 0.2%. The plates were incubated for 5 h at 37° C., 5% $CO_2$ to allow cells to attach to the bottom of the wells in the presence of the tested compounds. The media was removed and replaced with fresh media containing tested compounds at the same final concentration. The plates were incubated for 18 h at 37° C., 5% $CO_2$. Concentrations of Ab1-x were determined using AlphaLISA immunoassay (PerkinElmer, Cat. # AL288) following the manufacturer's protocol. Concentrations of Abeta1-x in the wells containing either DMSO or 10 µM beta-secretase inhibitor (BACE inhibitor IV, EMD Bioscience, Cat. #565788) were used as uninhibited and background controls, respectively, for calculating percent inhibition values for each well with the tested compounds. These percent inhibition values were regressed against compound concentrations using four-parameter curve fitting, and the IC50 values (concentration of a compound at which 50% of the inhibitory effect was observed) were calculated as the compound concentration corresponding to the inflection point on the curve.

Compounds of the invention were tested for BACE1 inhibitory potency as measured in assay 1, and for cellular inhibitory potency as measured in assay 2. The biological data are presented in Table 1, below.

TABLE 1

| Example | BACE 1 $IC_{50}$ nM (Assay 1) | Cell $IC_{50}$ nM (Assay 2) |
|---|---|---|
| 1 | 4.0 | 4.5 |
| 2 | 3.5 | 4.0 |
| 3 | 37 | 34 |
| 4 | 16.3 | 6.2 |
| 5 | 1.5 | 2.0 |
| 6 | 1.5 | 0.6 |
| 7 | 8.2 | 4.0 |

Table 2, below, demonstrates superiority of compounds of the present invention over certain compounds described in WO 2012/087237.

TABLE 2

Comparison Table

| | |
|---|---|
| Example 1<br>BACE 1 $IC_{50}$ = 4.0 nM | Example 19 of<br>WO 2012/087237<br>BACE 1 $IC_{50}$ = 53 nM |
| Example 2<br>BACE 1 $IC_{50}$ = 3.5 nM | Example 79 of<br>WO 2012/087237<br>BACE 1 $IC_{50}$ = 188 nM |
| Example 4<br>BACE 1 $IC_{50}$ = 16.3 nM | Example 19 of<br>WO 2012/087237<br>BACE 1 $IC_{50}$ = 53 nM |
| Example 6<br>BACE 1 $IC_{50}$ = 1.5 nM | Example 20f of<br>WO 2012/087237<br>BACE 1 $IC_{50}$ = 5.5 nM |

The invention claimed is:

1. A compound of Formula I:

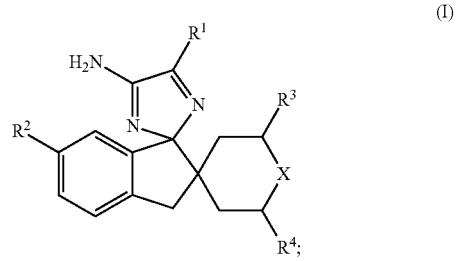

or a pharmaceutically acceptable salt thereof, wherein:
$R^1$ is $C_{1-6}$ alkyl optionally substituted with one or more halogen atoms;
$R^2$ is H, halo, —CN, —OH, aryl, heteroaryl, $C_{1-6}$ alkyl, $C_{2-6}$ alkenyl or $C_{2-6}$ alkynyl, which latter five groups are optionally substituted with one or more groups independently selected from $C_{1-6}$ alkyl, halo, —CN, cycloalkyl, $C_{1-6}$ haloalkyl, —$OC_{1-6}$ alkyl, $C_{2-6}$ alkenyl, $C_{2-6}$ alkynyl and —$OC_{1-6}$ haloalkyl;
O-aryl or —O-heteroaryl each of which are optionally substituted with one or more groups independently selected from halogen, —CN and $C_{1-6}$ alkyl; or
NHCO-heteroaryl optionally substituted with one or more groups independently selected from halo, —CN, —O—$C_{1-6}$ alkyl, $C_{1-6}$ alkyl and $C_{1-6}$ haloalkyl;
$R^3$ and $R^4$ are each independently —H, halo, —CN, —O—$C_{1-6}$ alkyl, or $C_{1-6}$ alkyl wherein the $C_{1-6}$ alkyl represented by R³ and R⁴ is optionally substituted with one or more halogen atoms, with the proviso that R³ and R⁴ cannot both be —H;

X is —O—, —S(O)—, —S(O)₂—, —C(O)—, —NRᵃ— or —C(R⁵R⁶)—;

Rᵃ is —H or $C_{1-6}$ alkyl;

R⁵ and R⁶ are each independently H, halo, —CN, —OR⁷ or $C_{1-6}$ alkyl, wherein the $C_{1-6}$ alkyl represented by R⁵ and R⁶ is optionally substituted with one or more halogen atoms; and R⁷ is H or $C_{1-6}$ alkyl.

2. The compound of claim 1, wherein the compound is of Formula (II):

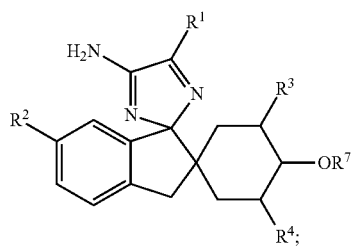

or a pharmaceutically acceptable salt thereof.

3. The compound of claim 1, wherein the compound is of Formula (IIa):

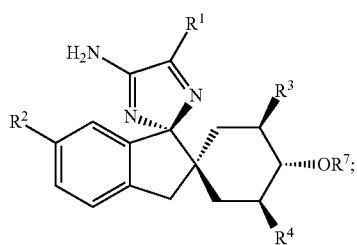

or a pharmaceutically acceptable salt thereof.

4. The compound of claim 1, wherein:

R³ and R⁴ are each independently —H or $C_{1-4}$ alkyl, with the proviso that R³ and R⁴ cannot both be —H; and R⁷ is —H or $C_{1-4}$ alkyl.

5. The compound of claim 4, wherein:

R³ and R⁴ are each independently H, methyl or ethyl, with the proviso that R³ and R⁴ cannot both be —H; and R⁷ is —H or methyl.

6. The compound of claim 5, wherein:

R² is —CN, halo, phenyl or a 6 membered heteroaryl, which two latter groups are optionally substituted with one or more groups selected from halo, —CN, $C_{1-6}$ alkyl, $C_{2-6}$ alkenyl and $C_{2-6}$ alkynyl; or —NHC(O)-(6 membered heteroaryl) optionally substituted with one or more halo groups.

7. The compound of claim 6, wherein:

R² is —CN, halo, phenyl or pyridyl which latter two groups are optionally substituted with one or more groups selected from halo, —CN, $C_{1-6}$ alkyl, $C_{2-6}$ alkenyl or $C_{2-6}$ alkynyl; or —NHC(O)-pyridyl optionally substituted with one or more halo groups.

8. The compound of claim 7, wherein:

R² is —CN, halo or pyridinyl, the latter group of which is optionally substituted with halo or $C_2$- alkynyl; or —NHC(O)-pyridyl optionally substituted with halo.

9. The compound of claim 8, wherein R² is —CN or halo.

10. The compound of claim 1, wherein the compound is selected from:

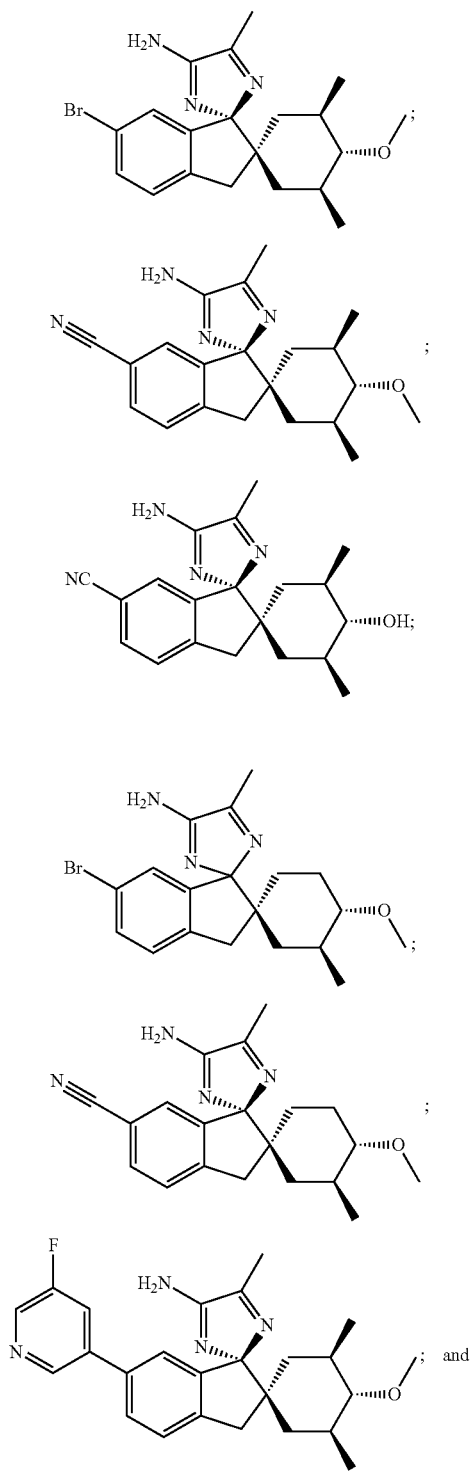

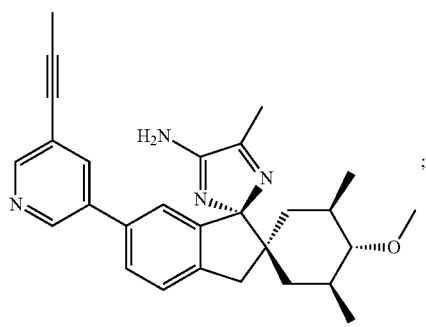
or a pharmaceutically acceptable salt of any of the foregoing.
11. The compound of claim 1, wherein the compound is selected from:
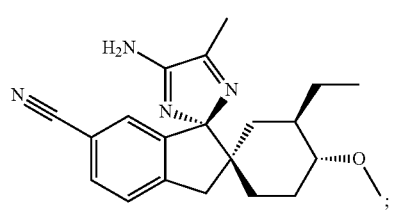 [SMILES: CC[C@@H]1C[C@]2(CC[C@H]1OC)Cc1ccc(C#N)cc1[C@@]21N=C(C)C(N)=N1]
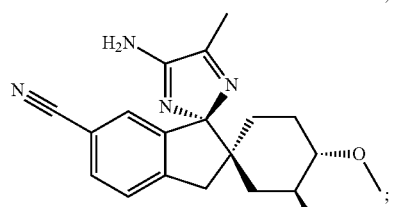
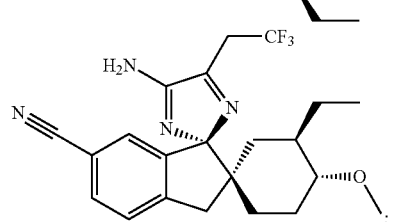
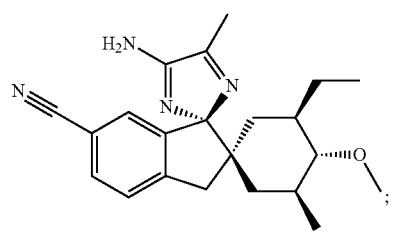
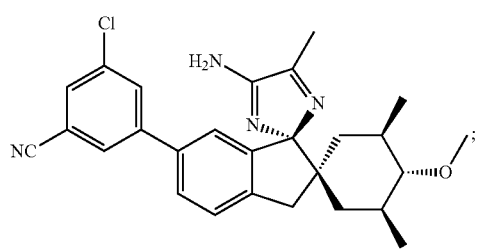
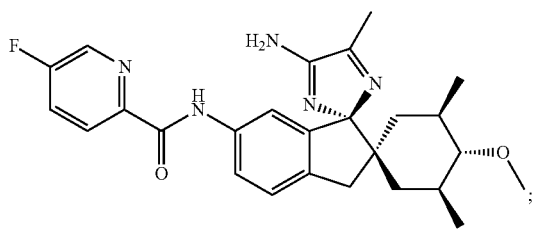
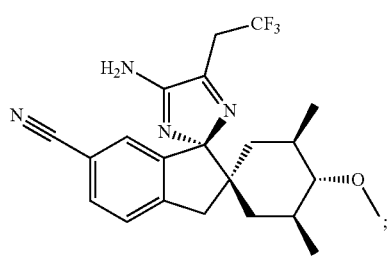
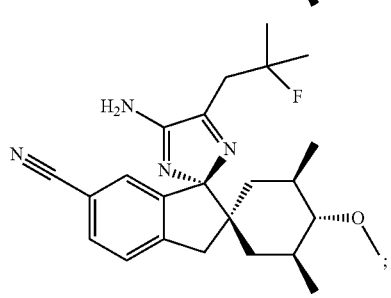
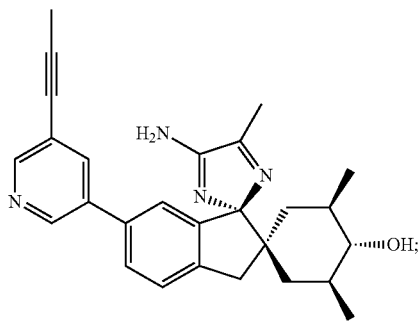
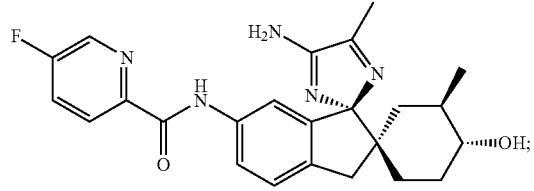
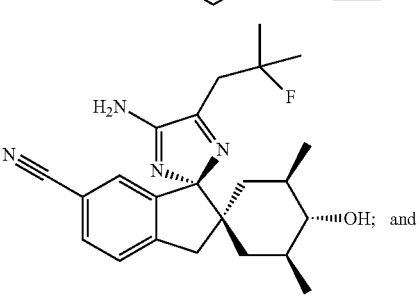

-continued

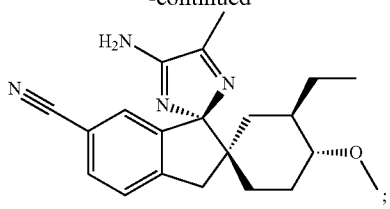

or a pharmaceutically acceptable salt of any of the foregoing.

12. A pharmaceutical composition comprising a compound of claim 1, or a pharmaceutically acceptable salt thereof, and a pharmaceutically acceptable carrier.

13. A method of treating a BACE1 mediated-disease or disorder in a subject, wherein the disorder or disease is selected from the group consisting of Alzheimer's disease, glaucoma, Down's Syndrome, HCHWA-D, cognitive impairment and cognitive decline, comprising administering to the subject an effective amount of a compound of claim 1, or a pharmaceutically acceptable salt thereof.

14. The method of claim 13, wherein the disease or disorder is Alzheimer's disease.

15. The method of claim 13, wherein the disease or disorder is glaucoma.

16. The method of claim 13, wherein the disease or disorder is Down's Syndrome.

17. The method of claim 13, wherein the disease or disorder is HCHWA-D.

18. The method of claim 13, wherein the disease or disorder is cognitive impairment or cognitive decline.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Glu Val Asn Leu Asp Ala Glu Phe Lys
1               5
```